(12) United States Patent
Tretheway et al.

(10) Patent No.: US 8,961,751 B2
(45) Date of Patent: Feb. 24, 2015

(54) ELECTROCHEMICAL LIQUID TREATMENT CELL WITH MODULAR CONSTRUCTION

(75) Inventors: James A. Tretheway, Madison, WI (US); Myron F. Miller, Sacramento, CA (US); Karl W. Marschke, Madison, WI (US); Brian R. Hale, Lake Mills, WI (US); Ajit K. Chowdhury, Madison, WI (US); Jeremy J. Vogel, Fort Atkinson, WI (US)

(73) Assignee: Biolonix, Inc., McFarland, WI (US)

( * ) Notice: Subject to any disclaimer, the term of this patent is extended or adjusted under 35 U.S.C. 154(b) by 267 days.

(21) Appl. No.: 12/895,253

(22) Filed: Sep. 30, 2010

(65) Prior Publication Data

US 2011/0079510 A1    Apr. 7, 2011

Related U.S. Application Data

(60) Provisional application No. 61/248,077, filed on Oct. 2, 2009.

(51) Int. Cl.
*C25C 7/00* (2006.01)
*C25C 7/02* (2006.01)
(Continued)

(52) U.S. Cl.
CPC ............... *C02F 1/4672* (2013.01); *A23L 3/325* (2013.01); *A61L 2/035* (2013.01); *C02F 1/46104* (2013.01); *C02F 1/4674* (2013.01);
(Continued)

(58) Field of Classification Search
CPC .............. C25C 7/00; C25C 7/02; C25B 9/00; C25B 9/02; C25B 11/02

USPC ........ 204/269, 280, 288, 288.2, 288.4, 288.5, 204/289
See application file for complete search history.

(56) References Cited

U.S. PATENT DOCUMENTS 1,420,037 A * 6/1922 Harris ........................... 204/258
3,725,226 A   4/1973 Stoner
(Continued)

FOREIGN PATENT DOCUMENTS

EP    066 938 A2   12/1982
EP    0452597 A1   10/1991
(Continued)

OTHER PUBLICATIONS

Atashi, Shara, PCT International Search Report and the Written Opinion of the International Searching Authority for PCT/US2010/051093 dated Feb. 15, 2011, European Patent Office, Rijswijk, Netherlands.
(Continued)

*Primary Examiner* — Zulmariam Mendez
(74) *Attorney, Agent, or Firm* — Boyle Fredrickson, S.C.

(57) ABSTRACT

A cell for direct treatment of liquid using electrolysis uses a modular construction of electrode plates and spacer assemblies positioned between end plates. Changes in the liquid flow capacity of the cell may be made by changing the number of module housing sections and electrode plate assemblies. The design includes electrode plates that lock into a mating module housing section to resist the pressure of the fluid being treated. The design further provides for multiple fluid flow paths and for automatic cleaning of the cell using standard clean-in-place methods.

19 Claims, 9 Drawing Sheets

(51) Int. Cl.

| | |
|---|---|
| *C25B 9/00* | (2006.01) |
| *C25B 9/02* | (2006.01) |
| *C25B 11/02* | (2006.01) |
| *C02F 1/467* | (2006.01) |
| *A23L 3/32* | (2006.01) |
| *A61L 2/03* | (2006.01) |
| *C02F 1/461* | (2006.01) |
| *C02F 101/30* | (2006.01) |
| *C02F 103/22* | (2006.01) |
| *C02F 103/32* | (2006.01) |
| *C02F 103/34* | (2006.01) |
| *C02F 103/42* | (2006.01) |

(52) U.S. Cl.
CPC ........... C02F 2001/46142 (2013.01); *C02F 2101/305* (2013.01); *C02F 2103/22* (2013.01); *C02F 2103/32* (2013.01); *C02F 2103/343* (2013.01); *C02F 2103/42* (2013.01); *C02F 2201/003* (2013.01); *C02F 2201/4611* (2013.01); *C02F 2201/46115* (2013.01); *C02F 2201/4613* (2013.01); *C02F 2209/04* (2013.01); *C02F 2209/06* (2013.01); *C02F 2209/29* (2013.01); *C02F 2301/043* (2013.01); *C02F 2301/046* (2013.01); *C02F 2303/04* (2013.01); *Y02E 60/366* (2013.01)
USPC ........ 204/269; 204/280; 204/288; 204/288.2; 204/288.4; 204/288.5; 204/289

(56) References Cited

U.S. PATENT DOCUMENTS

| | | | |
|---|---|---|---|
| 4,384,943 A | 5/1983 | Stoner et al. | |
| 4,479,864 A | 10/1984 | Kanai et al. | |
| 4,743,350 A | 5/1988 | Cawlfield et al. | |
| 4,892,636 A | 1/1990 | Bolick, II et al. | |
| 5,034,110 A | 7/1991 | Glore et al. | |
| 5,322,604 A | 6/1994 | Cawlfield | |
| 5,766,431 A | 6/1998 | Tanaka et al. | |
| 6,733,654 B1 | 5/2004 | Itzhak | |
| 7,241,390 B2 | 7/2007 | Lyles, III | |
| 7,335,284 B2 | 2/2008 | Haenni et al. | |

FOREIGN PATENT DOCUMENTS

| | | |
|---|---|---|
| EP | 0627386 A1 | 12/1994 |
| EP | 1 698 594 A1 | 9/2006 |
| GB | 2257984 A | 1/1993 |
| WO | WO 01/17910 A1 | 3/2001 |

OTHER PUBLICATIONS

Patermarkis, G., et al,, Disinfection of Water by Electrochemical Treatment, Water Res., vol. 24, No. 12, pp. 1491-1496, 1990, Pergamon Press, Oxford, UK.

Stoner, G.E., et al., The Mechanism of Lower Frequency a.c. Electrochemical Disinfection, Biolelectrochemistry and Bioenergetics 9 (1982) pp. 229-243, A section of J. Electroanal Chem. and constituting vol. 141 (1982), Elsevier Sequoia S.A., Lausanne, Switzerland.

Ye., J., et al., Inactivation of *Listeria monocytogenes* in Recirculated Brine for Chilling Thermally Processed Bacon Using Electrochemical Treatment System, vol. 66, No. 5, 2001, pp. 729-733, Journal of Food Science, Institute of Food Technologists, Chicago, IL, USA.

Li, Y., et al., Inactivation of *Listeria* in Recirculated Chilling Brine Using Flow-Through Electrolyzing Treatment, pp. 1-8, Written for presentation at the 2004 CIGR International Conference, Sponsored by CIGR, CSAM and CSAE, Beijing China Oct. 11-14, 2004.

Kraft, A., Electrochemical Water Disinfection: A Short Review, Platinum Metals Review, 2008, 52, (3), pp. 177-185, Johnson Matthey PLC, Royston, Herfordshire, UK.

\* cited by examiner

ELECTROCHEMICAL LIQUID TREATMENT CELL WITH MODULAR CONSTRUCTION

CROSS-REFERENCE TO RELATED APPLICATIONS

This application claims the benefit of U.S. Provisional Application 61/248,077 filed Oct. 2, 2009 hereby incorporated by reference.

BACKGROUND OF THE INVENTION

The present invention relates to a flow-through cell for the treatment of liquid streams using electrochemical liquid treatment (electrolysis) and, in particular, to a treatment cell having a modular plate design readily adapted to different flow rates. Liquid treatment may include disinfection or oxidation of biological or chemical species, or other use for which electrolysis is appropriate, such as electroflocculation or electrowinning. Electrolysis includes but is not limited to methods using direct current, alternating current, switched direct current, or pulsed power.

Electrochemical liquid treatment systems have been used in a variety of industries for different applications. Chlorine gas and caustic soda are produced commercially by the electrolysis of highly concentrated salt water solutions (brine). Other systems electrolyze brine to produce hypochlorite, and this stream is then injected into another liquid to provide disinfection. Related systems may be used to directly disinfect low salinity swimming pool water as a replacement liquid chlorine disinfecting solutions.

In most cases this electrolytic treatment takes place in a flow-through treatment cell that in its simplest form is a housing with a liquid inlet and outlet, and containing two electrodes, one of which is an anode and the other a cathode. In most cases low voltage DC power is applied, but sometimes the polarity may be switched every several hours to help prevent electrode fouling. A new process provides for AC or switched DC electrochemical treatment. This invention applies to all such methods of electric power.

Until now most of these designs consisted of two or more electrodes, usually flat plates arranged in a stack with insulated separators between them. The housing was a separate shell containing one or more plate stacks and the liquid treatment volume. Flow rates and treatment volumes were limited to selected standard models or required custom fabrication. Little attention was placed on the cleanability and sanitation of the internal flow chamber and the electrode components, preventing its use in applications such as food, beverage and pharmaceutical processing.

SUMMARY OF THE INVENTION

The present invention provides an improved modular design for an electrolysis system that allows additional electrode plates and treatment channels to be readily added or removed depending on the application requirements. The ability to precisely tailor the number of electrode plates to the application can be important in ensuring the residence time necessary for effective treatment of the liquid and may significantly affect the electrical efficiency of the treatment process. The modular construction also permits the use of standard components to provide flow rates that precisely meet customer needs and the customer's ability to expand capacity to accommodate growth.

In addition, the design includes an innovative method to support the outer housing with the electrode plates themselves to counteract the outward pressure from the liquid contained in the treatment cell. Design elements also make the treatment cell suitable for automated cleaning without disassembly, called "clean-in-place or "CIP", a necessary requirement for use in applications with demanding sanitation requirements, such as those in the food, beverage and pharmaceutical industries.

Specifically then, the present invention provides a flow-through treatment cell for the electrolytic treating a liquid flow and having substantially planar first and second endplates together supporting at least one inlet port and one output port through an end plate. At least two electrode plates each having first and second opposed edge pairs are provided, and at least one module housing section having a central aperture provides an inner lip receiving the first opposed edge pair of at least one electrode plate against the lip and exposes the second electrode edge pair spanning a central aperture. A clamping means is attachable to the first and second end plates to assemble the system by drawing the end plates against a variable number of module housing sections positioned therebetween to provide a continuous channel for flow between the inlet port and the outlet port so that the flow divides to pass across the second electrode edge pairs of each electrode.

It is thus a feature of at least one embodiment of the invention to provide a liquid treatment system that may be readily tailored to a particular flow rate by changing the number of electrodes and module housing sections and adjusting the clamping means accordingly. It is also a feature of at least one embodiment of the invention to provide for the alignment and support of each section of the treatment cell via the clamping means.

The first and second end plates and module housing sections may be an electrically insulating material. In one embodiment the first and second end plates and the module housing sections are a polymer.

It is thus a feature of at least one embodiment of the invention to provide a design that ensures electrical insulation between the plates and that can also withstand substantial liquid pressure.

The use of a series of module housing sections allows efficient fabrication and stocking of components of the system while permitting an arbitrarily large treatment cell to be created using readily obtained and fabricated sheet materials.

The liquid treatment system may further include a set of gaskets providing apertures corresponding to the central aperture of the module housing sections and positionable between each of the module housing sections to seal between module housing sections and/or between module housing sections and end plates to prevent fluid leakage. These gaskets may also be designed to standards permitting automated CIP sanitation.

It is thus a feature of at least one embodiment of the invention to permit the construction of a modular system with practical manufacturing tolerances and to meet the requirements for CIP sanitation.

It is also important to shield the electrode plates to protect them from exterior contact with metal parts that could cause a short circuit, from plant washdown liquids that could corrode the plates and provide a path for current leakage to the exterior, and from contact with plant personnel to prevent possible electrical shock.

It is thus a feature of at least one embodiment of the invention to provide a secondary sealing means to insulate the electrode plates from exposure to external contact.

The liquid treatment system may include a means of attaching the first opposed edges of an electrode plate to a corresponding module housing section both to tension the second opposed edges of the electrode plate and to prevent the module housing section from deflecting outwards due to the pressure of the liquid inside.

It is thus a feature of at least one embodiment of the invention to provide an attachment means between the electrode plates and the modular housing sections whereby the electrode plates are stiffened by the pressure of the treatment liquid on the housing sections and these housing sections are prevented by the electrode plates from expanding outwards under the pressure of the treatment liquid.

One implementation of this attachment means is provided by bending the first opposed edges of an electrode plate so that the bent edges that fit into mating slots in the corresponding housing section.

It is thus a feature of at least one embodiment of the invention to have the attachment means for the electrode plate be a bent configuration of the first opposed edges of the plate.

Another implementation of this attachment means is two electrical busbars attached to the first opposed edges of an electrode plate that fits into mating slots in the corresponding module housing section. This implementation also provides improved current distribution through an electrode fabricated from thin plate material to maximize liquid flow volume.

It is thus a feature of at least one embodiment of the invention to have the attachment means for the electrode plate be two busbars attached to the first opposed edges of the plate.

The system may provide one or more electrical conductors extending outward from at least one busbar to extend beyond a wall of a module housing section surrounding the central aperture and to connect with one or more corresponding electrical terminals.

It is thus a feature of at least one embodiment of the invention to provide a simple and modular electrical interconnection system that accommodates the modularity of the electrical plates allowing each plate to be interconnected by an easily modifiable electrical harness.

The electrodes may include first and second electrode plates having electrical conductors attached at different locations to stagger the electrical terminals to two or more positions along an outer edge of the module housing sections for alternate electrode plates.

It is thus a feature of at least one embodiment of the invention to permit close spacing of the electrical plates without interference among the connectors and to provide a visual segregation between connector polarities.

The busbars may be held by bolts through corresponding apertures in walls of the module housing sections to attach the electrode plates to the module housing sections.

It is thus a feature of at least one embodiment of the invention to provide a robust physical attachment of the electrode plates to the module housing sections simplifying the assembly process.

The system may include a support frame providing a first set of horizontally extending rails supporting lower edges of the end plates and module housing sections and a second set of horizontally extending rails abutting vertical edges of the end plates and module housing sections.

It is thus a feature of at least one embodiment of the invention to provide an external skeletal structure providing additional resistance against pressure distending the assembly of the end plates and module housing sections.

The electrode plates are fabricated from an electrically conductive material including metals, metal oxides and doped diamond, some of which may act as process catalysts.

It is thus a feature of at least one embodiment of the invention to provide a system compatible with relatively thin metallic plates. It is further a feature of at least one embodiment of the invention to provide a system allowing ready access to the plates for cleaning.

The clamping means may be a multiple threaded bar passing through bores extending between the end plates and through walls of module housing sections positioned therebetween to clamp the end walls about the module housing sections through corresponding releasable nuts threadably received on the threaded bars.

It is thus a feature of at least one embodiment of the invention to provide a clamping system that is simple, adjustable, and that can provide distributed clamping forces compatible with construction of the housing of the system from insulating polymer materials or like.

The electrode plates are substantially parallel with a spacing of greater than 5 mm when the system is assembled.

It is thus a feature of at least one embodiment of the invention to provide a system suitable for direct use with liquid that may contain suspended solids and high viscosities.

The inlet and outlet ports may be positioned near opposite edges of a single end plate.

It is thus a feature of at least one embodiment of the invention to provide a system having proximate inlets and outlets permitting adjustment of the number of electrical plates without replumbing the ports to the system.

To accommodate more complex liquid distribution arrangements, both end plates may include inlet and/or and outlet ports.

It is thus a feature of at least one embodiment of the invention to provide a means to combine or distribute liquid streams flowing through the treatment cell.

Both end plates may include inlet and outlet ports combined with a solid separator plate within the modular assembly.

It is thus a feature of at least one embodiment of the invention to provide a means to treat two separate liquid streams in one treatment cell assembly.

These particular objects and advantages may apply to only some embodiments falling within the claims and thus do not define the scope of the invention.

DETAILED DESCRIPTION OF THE PREFERRED EMBODIMENT

Figure 1:
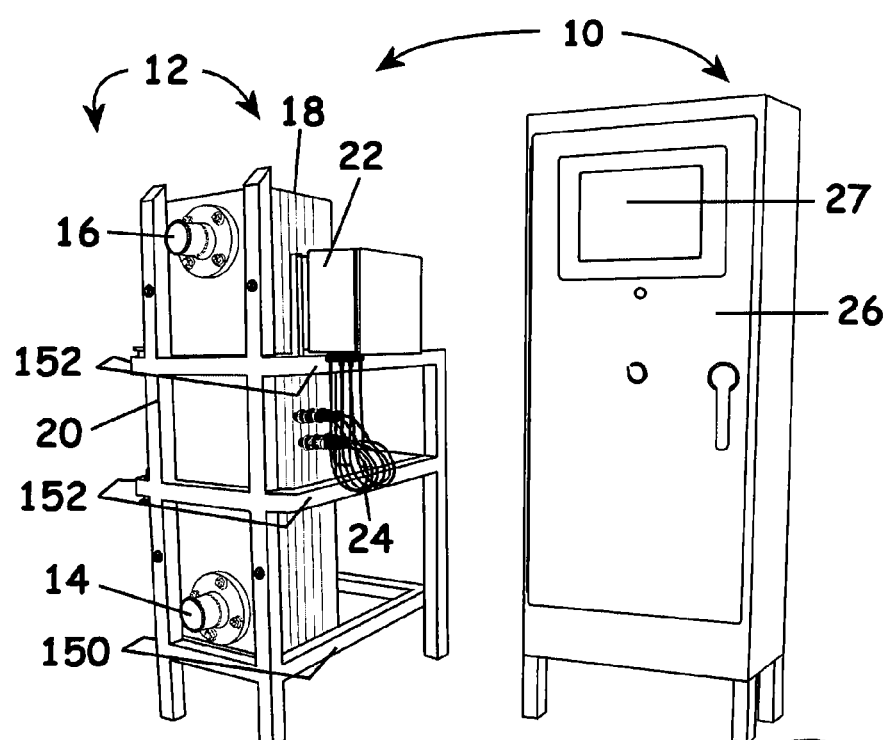
FIG. 1 is a perspective view of a liquid treatment system in one embodiment of the present invention showing a main housing holding opposed planar electrodes between liquid inlets and outlets, a power distribution module, and a control unit.
Figure 2:
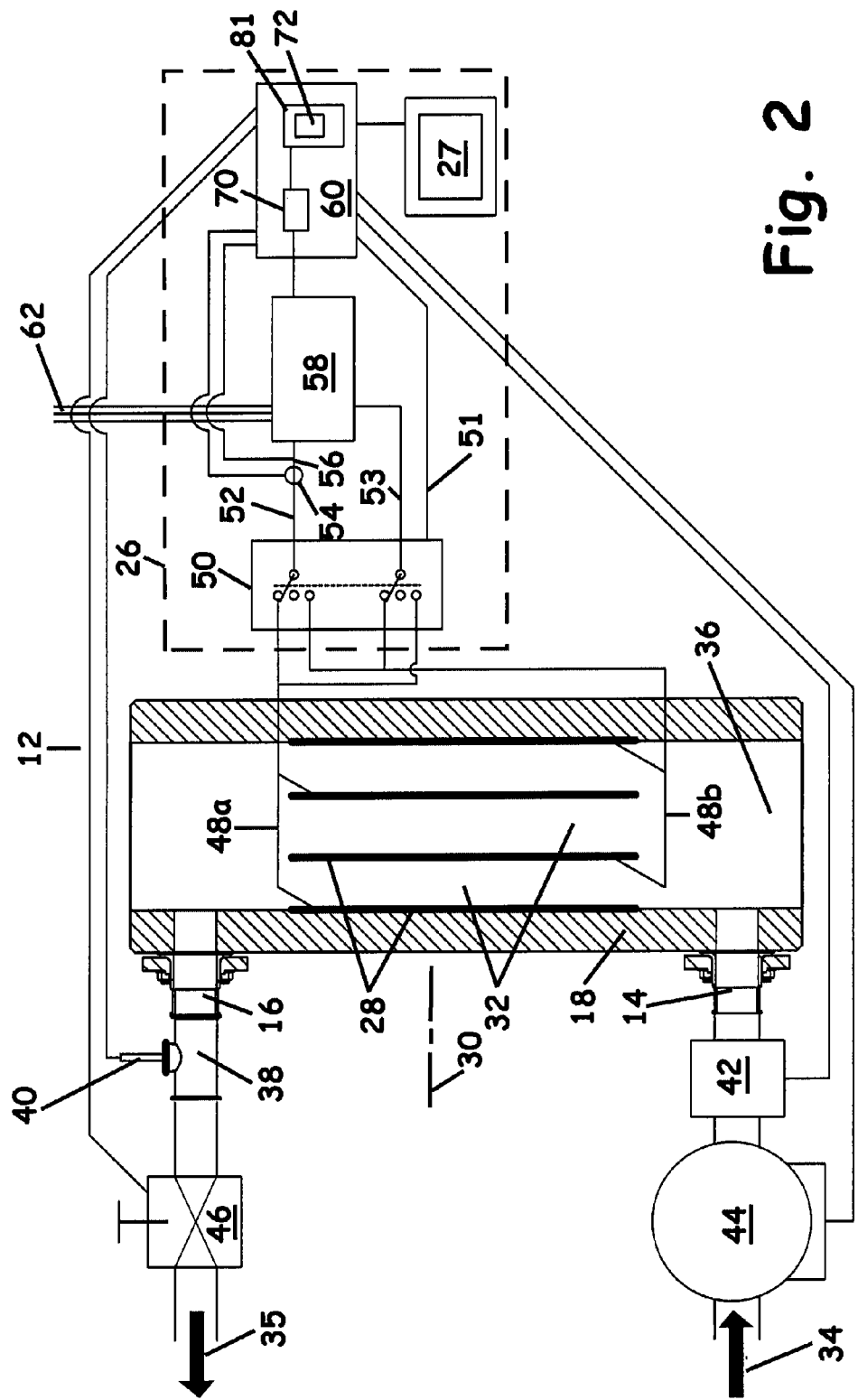
FIG. 2 is a detailed block diagram of the components of FIG. 1.

Referring now to FIGS. 1 and 2, a liquid treatment system 10 per the present invention may include a treatment unit 12 providing a liquid inlet 14 and outlet 16 to conduct liquid across internal plates 28. The plates 28 are contained in an insulating housing 18 supported on frame 20. A power distribution module 22 provides electrical connections 24 to the internally contained plates 28 for power received from a control unit 26. The control unit 26 has a touchscreen user interface 27 for the display and entry of data including critical operation parameters.

Referring now to FIG. 2, the treatment unit 12 includes two or more generally planar and parallel electrical plates 28 held in a channel 36 between the inlet 14 and the outlet 16. The plates 28 are separated along an axis 30 generally perpendicular to the flow of liquid by gaps 32 to receive liquid 34 therethrough. The separation of the plates 28 will be greater than 5 mm to permit the passage of untreated liquid 34 without undue risk of clogging.

One or more chemical sensors 40 may be positioned in sensor fitting 38 downstream from the plates 28 and channel 36 to measure chemical properties of the liquid and/or a flow sensor 42 may be positioned in the stream of liquid 34 to measure the flow across the plates 28. The chemical sensors 40 may include those measuring pH, oxidation-reduction potential, chlorine level, free chlorine level, or total chlorine level.

The amount of flow through the channel 36 may be controlled by electrically driven pump 44 and/or valve 46 alone or in combination.

The plates 28 are electrically isolated from each other as held by the housing 18 but may be joined by the connections 24 from power distribution module 22 so that some or all of the plates 28 are electrically connected to electrical conductors 48a and 48b. In some configurations alternating electrode plates may be connected to opposite power polarities, in others some plates may not be directly connected to the power supply but instead become electrically activated by the ionic currents in the liquids being treated, resulting in each side of such intermediate plates having opposite polarities. The electrical conductors 48a and 48b are connected to a switching unit 50 that is part of the electrochemical process.

The controller 60 includes a processor 70 and a control program 72, the latter contained in the memory 81 communicating with the processor 70 as is generally understood in the art. In operation, the program 72 will read various parameters of the process including the plate current from current sensors 54, the plate voltage from voltage sensing points 56, user entered parameters through touchscreen 27, chemical environment sensing from the chemical sensor 40, and/or the flow rate from the flow sensor 42, and will provide output signals on control line 51 controlling the switching unit 50 and the power supply 58. In addition, output signals controlling the pump 44 and valve 46 and providing information on touchscreen 27 may be provided.

Figure 3:
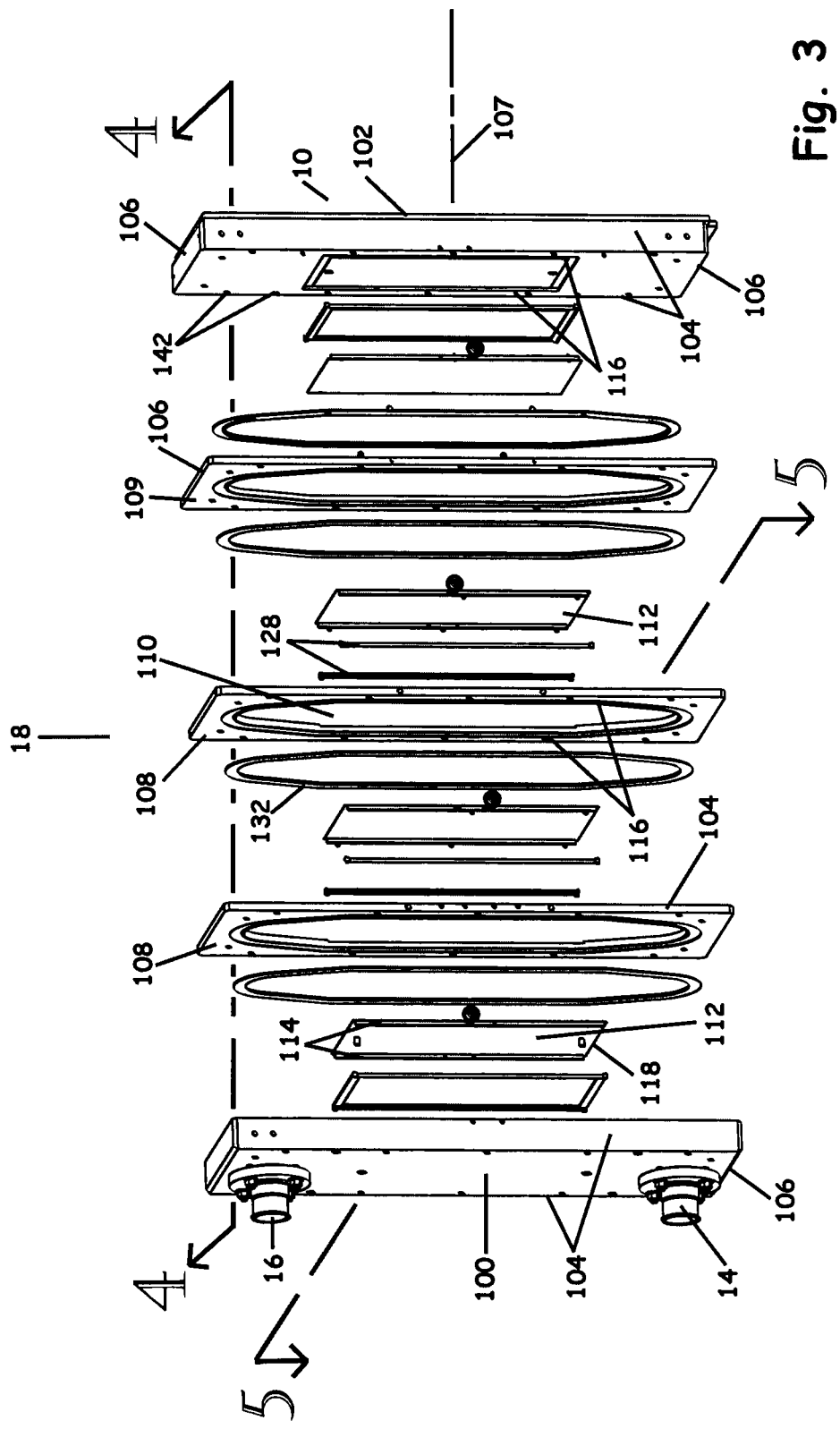
FIG. 3 is an exploded orthogonal view of the present invention showing modular components.

Referring now to FIG. 3, the housing 18 of the liquid treatment system 10 may be composed of first and second end plates 100 and 102 each being substantially planar and having parallel side walls 104 and top and bottom walls 106 describing long and short sides of a rectangular periphery of the plates 100 and 102. The plates 100 and 102 may be arranged to be substantially parallel to each other and separated along an axis 107 normal to their broad faces. Each of the endplates will have vertical lips 116 to receive vertical opposed edges 114 of electrode plates 112 aligned with the apertures 110 of the modular housing sections 108, both described below.

One or more module housing sections 108, having top and bottom walls 106 and vertical walls 104 and thus conforming to the periphery of the end plates 100 and 102, may be aligned with and positioned between the end plates 100 and 102. These module housing sections 108 provide a central aperture 110 large enough to allow passage of the treatment liquid from the inlet 14 and to the outlet 16 either directly or through a corresponding aperture 110 of another module housing section 108.

Module housing section 109 is similar to the module housing sections 108 except that it does not receive an electrode plate 112 but serves simply as a spacer between the electrode plate 112 on the end plate 102 adjacent to the module housing section 109 and the electrode 112 on the module housing section 108 closest to the end plate 102 on the other side of module housing section 109.

Electrode plates 112 may be positioned within the apertures 110 so that vertical opposed edges 114 (as shown) are supported by corresponding vertical lips 116 of the aperture 110 while the opposed horizontal edges 118 of the electrode plates 112 span the aperture 110. The electrode plates 112 may have surfaces of metal or metal oxides and may include catalytic surfaces.

Figure 4:
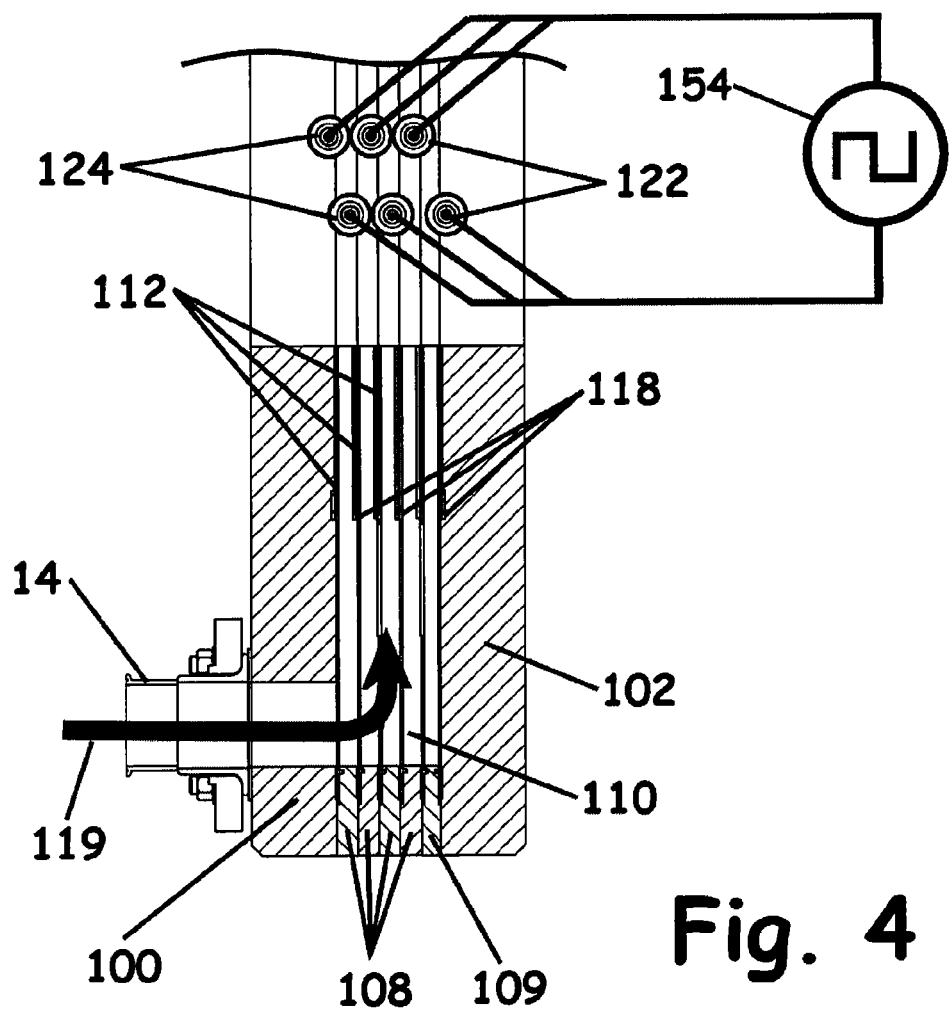
FIG. 4 is a simplified cross-section of three modular housing sections viewed along line 4-4 of FIG. 3 showing support of the internal electrical plates to divide liquid flow among them and a staggering of associated electrical connectors.

Referring now to FIG. 4, liquid flow 119 from the inlet 14 may pass through the apertures 110 to cross the horizontal edges 118 of the electrode plates 112 as it flows between the electrode plates 112 to the outlet 16 (not shown in FIG. 4).

Figure 5:
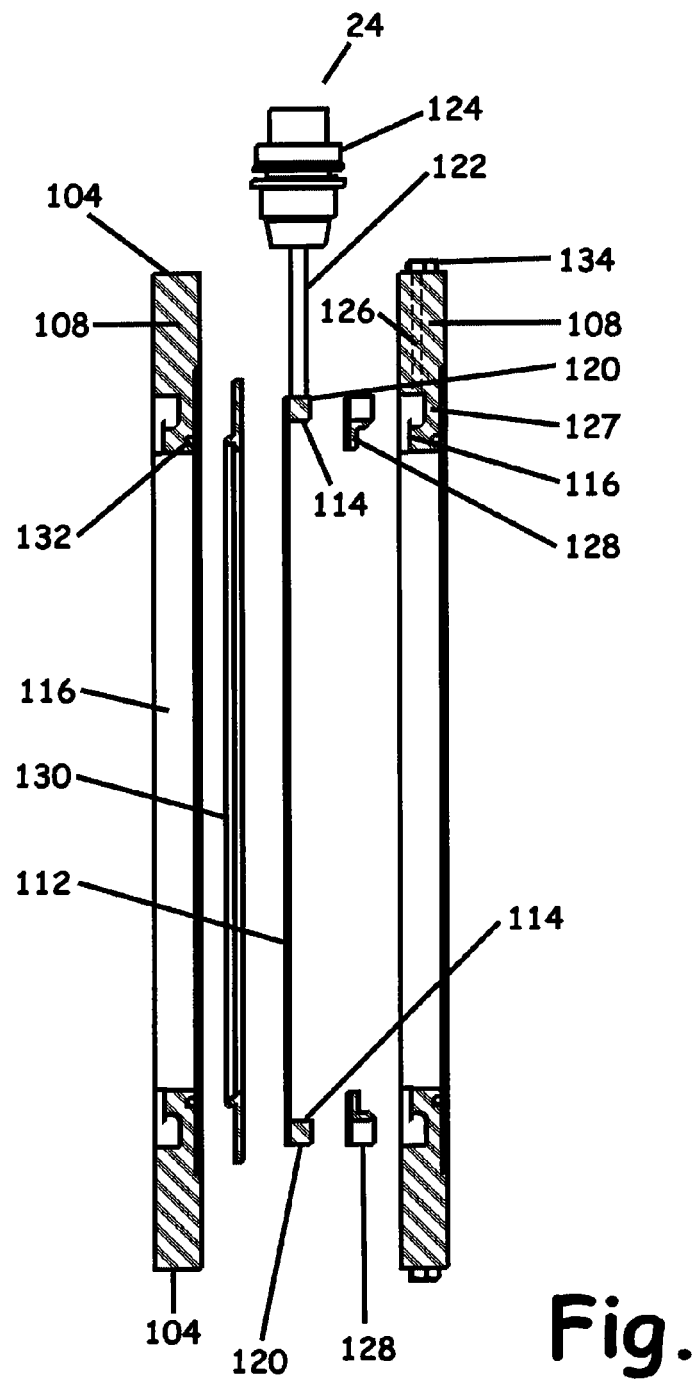
FIG. 5 is an enlarged cross-sectional view of two module housing sections and an electrode plate taken along lines 5-5 of FIG. 3.

Referring now to FIG. 5, each electrode plate 112 may have a busbar 120 of substantially square cross-section and of greater thickness along axis 107 than the electrode plate 112 attached to the vertical edges 114 of the electrode plates 112, for example, by brazing or welding to make electrical communication therewith.

The busbar 120 on one vertical edge 114 may also attach to one or more conductors 122 passing outwardly along the plane of the electrode plate 112 through one or more holes 126 in a vertical wall 104 of a corresponding module housing section 108. The conductor 122 may lead to an electrical connector 124 providing one of the connections 24 shown in FIG. 1.

The busbars 120 provide for improved distribution of current through the electrode plate 112 as fed by a single centrally located conductor 122 and stiffen and retain the electrode plates 112 within the module housing sections 108. In this latter capacity, the busbar 120 may be received in a corresponding groove 127 on an inner face of the module housing section 108 as sealed by a strip gasket 128. Standoffs 134 may be attached to the vertical wall 104 of the module housing section 108 to bear against the support frame 20 to minimize contact area and crevices where dirt or pathogens could accumulate.

An opposed surface of the electrode plate 112, displaced from the side attached to the busbar 120, may be sealed by a ring gasket 130 received by corresponding retaining groove 132 in an opposed face of the module housing section 108. Together the gaskets 130 and 128 prevent liquid leakage out of the housing 18 from a cavity formed by the combination of the apertures 110 of the module housing sections 108. Gasket 130 also provides a secondary seal for gasket 128 and at the same time prevents exterior wash down water and other contaminants from contacting electrode plate 112.

Figure 6:
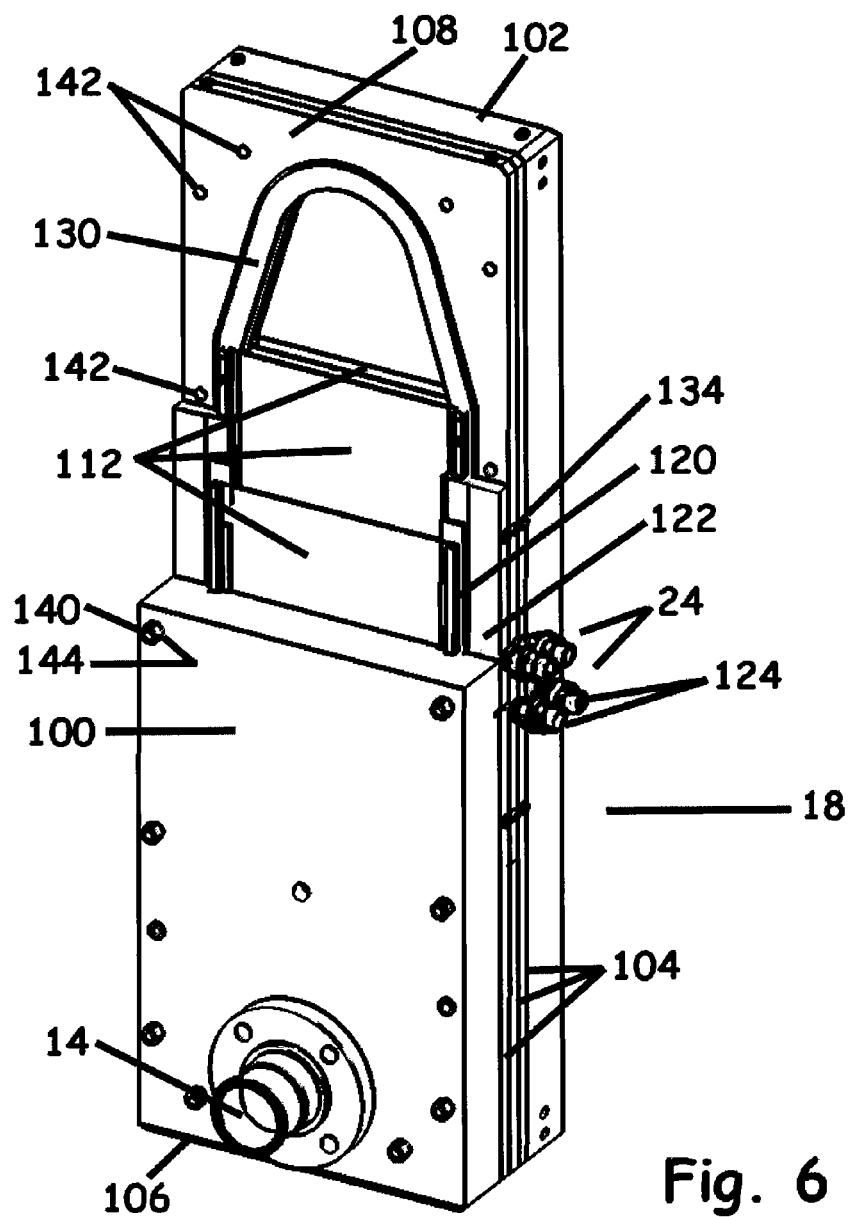
FIG. 6 is a partial cutaway of an assembled liquid treatment system of FIG. 3 having four electrical plates.

Referring now to FIG. 6, the housing 18 may be assembled by clamping the end plate 100 to the end plate 102 to sandwich multiple module housing sections 108, gaskets 128 and 130, and electrode plates 112 therebetween. A clamping means may be effected through the use of multiple threaded rods 140 passing through axially aligned bores 142 in the end plates 100, 102, and intervening module housing sections 108. Nuts 144 on exposed ends of the threaded rod 140 may be used to provide controlled compression of the end plates 100, 102 at multiple points to provide for a distributed and even compressive force without distortion or warping of the end plates 100, 102 and module housing sections 108.

Referring again to FIG. 1, the support frame 20 may provide for lower rails 150 supporting the bottom wall 106 of the end plates 100, 102 and module housing sections 108 and side rails 152 pressing inward on the vertical walls 104 of the module housing sections 108 to resist outward distention of the polymer materials caused by internal pressure.

Referring again to FIG. 4, the conductors 122 and connectors 124 may be staggered vertically along the edges of the electrode plates 112 so as to provide for closer plate spacing without interference between the connectors 124 and to segregate the connectors 124 according to their relative polarity during each excitation period when an AC power source 154 (formed by power supply 58 and switching unit 50 of FIG. 2) is applied across the connectors on 24 as depicted.

Figure 7:
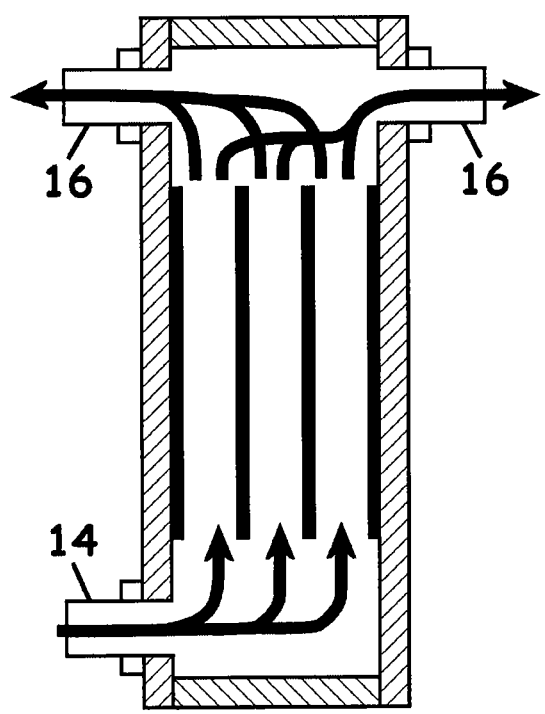
FIG. 7 is a diagram illustrating liquid flow with one inlet port and two outlet ports.

Referring now to FIG. 7, the flow from one inlet 14 may be distributed across two outlets 16.

Figure 8:
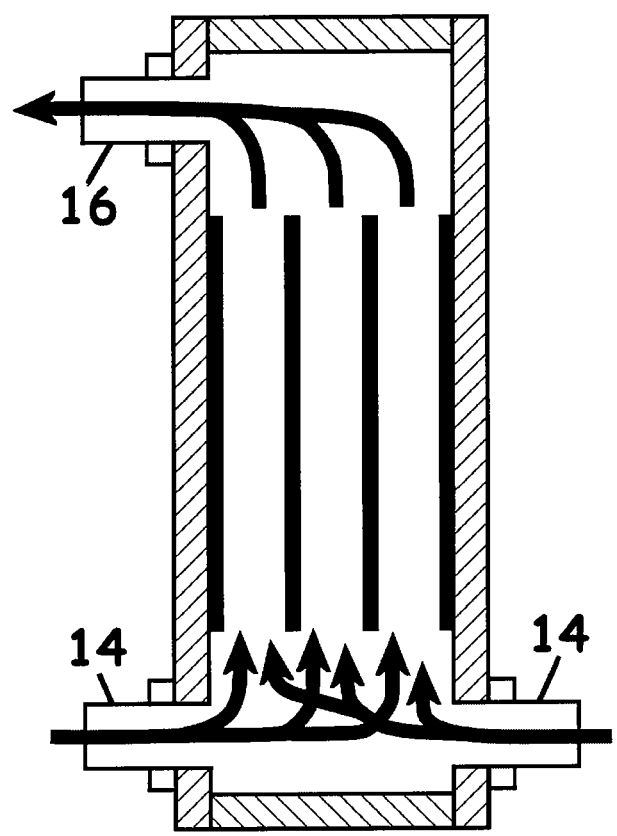
FIG. 8 is a diagram illustrating liquid flow with two inlet ports and one outlet port.

Referring now to FIG. 8, the flow from two inlets 14 may be combined into one outlet 16.

Figure 9:
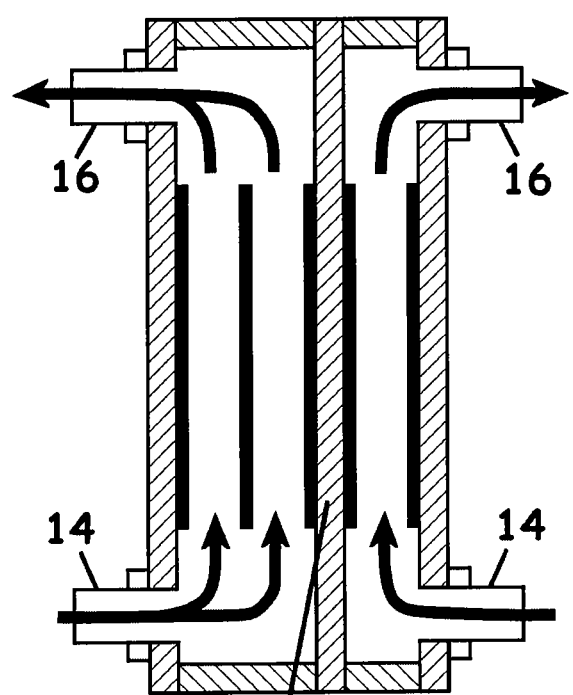
FIG. 9 is a diagram illustrating liquid flow with two inlet ports and two outlet ports along with a divider to treat two separate liquid streams in one treatment cell assembly.

Referring now to FIG. 9, two different liquid streams may be treated in one treatment cell assembly, with divider 200 separating the two liquid streams, each with one or more inlets 14 and outlets 16.

The present invention has been described in terms of the preferred embodiment, and it is recognized that equivalents, alternatives, and modifications, aside from those expressly stated, are possible and within the scope of the appending claims.

We claim:

1. A liquid treatment cell for treating a liquid flow, the cell comprising:
    a substantially planar first and second end plate together supporting at least one inlet port and one outlet port through an end plate;
    at least two electrode plates with at least one electrically conductive planar surface each having a periphery having first and second opposed edge pairs, with the first edge pair containing an interlocking element;
    at least one modular housing section providing a central aperture and composed of an insulating polymeric material in a rim around the central aperture, the rim receiving the interlocking element of a first electrode plate to resist relative movement of the rim of the modular housing section and first electrode plate from radial expansion of the rim about the aperture along a plane of the electrode plate, the interlocking element of the first electrode plate configured to limit outward deflection of the module housing section due to the pressure of the liquid inside the modular housing section, the modular housing section also abutting a second electrode plate to provide a channel of at least 5 mm wide through which liquid can flow between the electrode plates;
    at least one clamping element attachable to the first and second end plates to assemble a treatment system by drawing the end plates against a variable number of module housing sections positioned therebetween to assemble the insulating polymeric material of the modular housing sections together to provide a closed continuous channel for a flow between the inlet port and outlet port without leakage between modular housing sections with pressure of contained liquid so that the flow divides to pass between electrodes; and wherein the central aperture has an area no less than an area of the first electrode plate exposed to liquid flow, and wherein the first electrode plate is exposed to liquid flow through the aperture to the first electrode plate.

2. The liquid treatment cell of claim 1 wherein the central aperture of the modular housing sections has a greater area than a planar area of the electrode plates to provide an internal opening above and below the electrode plates communicating with the inlet port and outlet port respectively.

3. The liquid treatment cell of claim 1 further including at least one gasket providing an aperture corresponding to the central aperture of the module housing section and positionable between multiple module housing sections.

4. The liquid treatment cell of claim 1 further including at least one gasket providing a sealing perimeter between modular housing sections and fully surrounding an electrode plate to prevent an electrical path through liquid between the modular housing sections from the electrode plate to an exterior of the liquid treatment cell.

5. The liquid treatment cell of claim 4 wherein the at least one gasket seals between an electrode plate interlocking element and the modular housing section.

6. The liquid treatment cell of claim 1 wherein at least one gasket seals the electrode plate to a module housing section.

7. The liquid treatment cell of claim 1 including at least one gasket fitting between an electrode plate and the end plates.

8. The liquid treatment cell of claim 1 further including a stand for supporting assembled electrode plates, modular housing section, and endplates on a floor surface and wherein at least one of the inlet and outlet ports are positioned to permit substantially all liquid to drain from the liquid treatment cell when the port is opened and the assembled electrode plates, modular housing section, and endplates are supported in the stand on the floor surface.

9. The liquid treatment cell of claim 1 wherein the electrode plates, modular housing section, and endplates are food safe materials.

10. The liquid treatment cell of claim 1 wherein the interlocking means are projections extending perpendicularly with respect a plane of the electrode plates on the first opposed edge pair of the electrode plates.

11. The liquid treatment cell of claim 1 wherein the interlocking means are metal bars attached to each of the first opposed edge pairs of the electrode plates.

12. The liquid treatment cell of claim 11 wherein second opposed edges of the electrode plates do not contact the modular housing sections to provide passageways on each side of the electrode plates and wherein the metal bars are attached to the first opposed edges contacting the modular housing sections.

13. The liquid treatment cell of claim 12 wherein at least one of the metal bars serves as a power connection point for the electrode plates.

14. The liquid treatment cell of claim 1 further including at least one electrical conductor extending outward from each of at least two electrode plates to extend beyond an exterior wall of a module housing section to connect with an electrical terminal.

15. The liquid treatment cell of claim 1 wherein the clamping means are multiple threaded bars passing through bores extending between the end plates and through walls of module housing sections positioned therebetween to clamp the end walls about the module housing sections through corresponding releasable nuts threadably received on the threaded bars.

16. The liquid treatment cell of claim 1 wherein the inlet and outlet ports are positioned near opposite edges of a single end plate.

17. The liquid treatment cell of claim 1 wherein both end plates contain at least one port.

18. The liquid treatment cell of claim 1 wherein both end plates contain inlet and outlet ports and including a separator blocking liquid flow between ports on opposite endplates.

19. The liquid treatment cell of claim 1 further including a power system applying electrical power to the electrode plates for electrolytic treatment of liquid streams flowing through the treatment cell.

* * * * *

UNITED STATES PATENT AND TRADEMARK OFFICE
CERTIFICATE OF CORRECTION

PATENT NO. : 8,961,751 B2  
APPLICATION NO. : 12/895253  
DATED : February 24, 2015  
INVENTOR(S) : James A. Tretheway It is certified that error appears in the above-identified patent and that said Letters Patent is hereby corrected as shown below:

TITLE PAGE

(73) ASSIGNEE:    Delete "Biolonix, Inc." and substitute therefor

-- BioIonix, Inc. --

Signed and Sealed this  
Second Day of June, 2015

Michelle K. Lee  
*Director of the United States Patent and Trademark Office*